United States Patent [19]

Ito et al.

[11] 3,947,514
[45] Mar. 30, 1976

[54] PROCESS FOR PREPARATION OF N,N-DIALKYL TOLUAMIDE

[75] Inventors: Masatomo Ito; Taketosi Naito, both of Yokohama, Japan

[73] Assignee: Showa Denko K.K., Tokyo, Japan

[22] Filed: Apr. 9, 1975

[21] Appl. No.: 566,312

[52] U.S. Cl. ............................................. 260/558 R
[51] Int. Cl.² ........................................ C07C 103/22
[58] Field of Search ................................. 260/558 R

[56] References Cited
UNITED STATES PATENTS

| | | | |
|---|---|---|---|
| 3,631,104 | 12/1971 | Haberman et al. | 260/558 R |
| 3,699,164 | 10/1972 | Fine et al. | 260/558 R |
| 3,825,596 | 7/1974 | Naito et al. | 260/558 R |

*Primary Examiner*—Arthur P. Demers
*Attorney, Agent, or Firm*—Sherman & Shalloway

[57] ABSTRACT

N,N-Dialkyl-m(or p)-toluamide can be produced by reacting m(or p)-tolunitrile with dialkylamine and water in the liquid phase in the presence of adipic acid as a catalyst.

4 Claims, No Drawings

PROCESS FOR PREPARATION OF N,N-DIALKYL TOLUAMIDE

This invention relates to a process for the preparation of N,N-dialkyl-m(or p)-toluamides, and more particularly to a process for the preparation of N,N-dialkyl-m(or p)-toluamides comprising reacting m(or p)-tolunitrile with a dialkylamine and water in the liquid phase in the presence of adipic acid as a catalyst.

It has hitherto been known that N,N-dialkyl-m-toluamides are useful compounds as agricultural agents and insecticides, and especially N,N-diethyl-m-toluamide is a very effective mosquito repellant. It has been recorded in the literature that these compounds can be prepared by the reaction of m-toluic acid chloride with dialkylamines.

U.S. Pat. Nos. 2,932,665 and 3,198,831 disclose improved processes for the preparation of N,N-diethyl toluamide by reacting toluic acid with diethylamine in the vapour phase. These processes are based on a dehydration reaction, and are carried out in the presence of a dehydrating catalyst. These processes, however, can hardly be satisfactory enough as commercial processes. One reason is that since the raw material toluic acid is solid at room temperature, problems occur in reaction operations unlike the case where the raw materials are liquid. Another reason is that the toluic acid may be obtained by hydrolyzing tolunitrile by the use of acid or alkali, but at that time a considerably large amount of acid or alkali is consumed, thus bringing about economical disadvantage.

A process for preparing N,N-dialkyltoluamides directly from tolunitrile unlike the above-mentioned earlier processes is disclosed in U.S. Pat. No. 3,825,596 issued on July 23, 1974 and originally filed under Ser. No. 256,116 on May 23, 1972 by the same applicants as the present application. The process for preparing N,N-dialkyl-meta(or para)-toluamides disclosed in this U.S. Patent comprises reacting meta(or para)-tolunitrile with a dialkylamine with the alkyl group containing 1 to 4 carbon atoms and water in the liquid phase at a temperature of 200° to 350°C. in the presence of a catalyst comprising at least one compound selected from the group consisting of hydrochloric acid, sulfuric acid, phosphoric acid, acetic acid, benzoic acid, meta-toluic acid, acetates and chlorides of copper, zinc, cadmium, mercury, nickel, cobalt and lead, hydrogen peroxide and benzoyl peroxide.

It has now been found by the same applicants as the above U.S. Patent that the desired N,N-dialkyltoluamides can be produced advantageously by performing the reaction in the same way as disclosed in the above patent except using adipic acid as a catalyst instead of the above-specified catalytic compounds. Adipic acid is an aliphatic dicarboxylic acid, and is not at all disclosed in the above U.S. Patent. The advantages of using adipic acid as a catalyst will be described later on in this specification.

The N,N-dialkyl-m(or p)-toluamide with the alkyl group containing 1 to 4 carbon atoms will be referred to hereinbelow as "toluamide", and m(or p)-tolunitrile, as tolunitrile, for brevity.

As disclosed in the above U.S. Patent, the method for preparing toluamide directly from tolunitrile by reacting tolunitrile with a dialkylamine and water has various commercial advantages. The starting material tolunitrile can be obtained cheaply as a by-product in the manufacture of, e.g., benzenedinitrile from xylene by an ammoxidation reaction. Since, it is liquid at room temperature unlike toluic acid, it can be handled, transported and weighed easily, and is industrially advantageous. The process has a further advantage that it does not require any preliminary step for the preparation of toluic acid or toluic acid chloride or any auxiliary raw materials which are required in the earlier known processes. In addition, in the process dialkylamine, trialkylamine or mixture thereof can be used as one of the starting materials, and the presence of a small amount of a monoalkylamine is allowable since it does not hamper the reaction. Industrially, alkylamines are produced by the reaction of the corresponding alcohols with ammonia, and the product is generally a mixture of dialkylamine and trialkylamine, containing a small amount of monoalkylamine. Accordingly, the process can use such industrial product without any modification.

The principal reaction in the process may be expressed by the following equation.

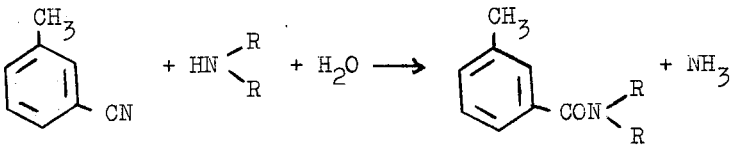

(wherein R is an alkyl radical). As shown above, the reaction is not a dehydration reaction, but water participates in the reaction as a reactant.

The present invention provides a process for the preparation of N,N-dialkyl toluamides which comprises reacting tolunitrile with a dialkylamine with the alkyl group containing 1–4 carbon atoms, and water at a temperature of 100°–400°C. in the liquid phase in the presence of adipic acid as a catalyst.

In the process, the reaction rate becomes too low if the temperature is less than 100°C., and the amount of an N-monoalkyl toluamide formed as a by-product increases if the temperature exceeds 400°C., and so these temperature are not desirable. The most preferable reaction temperature range is from 200° to 350°C. The pressure to be used is a pressure capable of maintaining the reactants in the liquid phase. Usually, the reaction is carried out under a pressure occurring spontaneously in correspondence to the reaction temperature applied, and this pressure somewhat changes with the progress of the reaction.

No critical limitation is placed on the ratio of the starting materials, but usually about 0.8–3 mols of the dialkylamine per mol of tolunitrile are used. If the amount of the dialkylamine is too small, unreacted tolunitrile is left behind. No harm is done if the amount of the dialkylamine is excessive, but no particular advantage is obtained even when the amount is more than 3 mols. It is preferable to use 1–2 mols of the dialkylamine per mol of tolunitrile. Water, the other starting material, is usually used in an amount of 0.8–5 mols per mol of tolunitrile. If the amount of water is too small, the reaction rate decreases and unreacted tolunitrile remains, and if it is excessive, the amount of by-product toluamide increases. The preferably amount of water to be used is 1–2.5 mols per mol of tolunitrile.

These catalysts act effectively even in a small amount, and it suffices if they are present in an amount of about 0.001–15 mol % based on the starting tolunitrile. No special advantage is obtained if they are used in excess. Usually, it is preferable to use them in an amount of 0.1–10 mol % based on the tolunitrile.

The commercial advantages of using adipic acid as a catalyst are as follows: As is well known, adipic acid is a non-toxic stable substance easily available at a relative low cost, and its handling is easy and does not involve risk. Furthermore, since it is a very weak acid, it is not likely at all to corrode the reaction apparatus. Another important advantage is that when adipic acid is used as a catalyst, the desired toluamide can be very easily separated from the reaction mixture after the reaction. The separation of the desired toluamide is usually performed by distillation of the reaction mixture. The adipic acid and adipic amides which may be formed by the reaction of a part of the adipic acid with a part of the starting dialkylamine are not distilled at the distilling temperature of the toluamide, but remain in the distillation still. Accordingly, neither adipic acid nor a by-product derived from it is mixed in the distilled toluamide.

It has been discovered also that according to the present invention, the reaction rate is increased and the desired N,N-alkyl toluamides can be produced in still higher yields by reacting tolunitrile with the dialkylamine and water while removing ammonia formed with the progress of the reaction from the reaction system.

The ammonia may be removed intermittently or continuously during the progress of the reaction, and since ammonia has the highest partial pressure of all the reactants and products, it is easy to remove it alone while keeping it gaseous from the reaction system. For example, if only the reaction vessel is cooled from the outside at certain intervals of time during the progress of the reaction and then on exhaust valve attached to the reactor is opened, a greater part of the ammonia formed till then is easily removed from the reactor in gaseous form. Then, the exhaust valve is closed and the reactor is heated again to a predetermined temperature, and the reaction is continued. Thus, the reaction and the removal of ammonia can be repeated alternatingly. Or ammonia may be removed continuously during the progress of the reaction through an exhaust valve or nozzle attached to the reactor. In this case, care must be taken so that the exhaust valve or nozzle may be opened narrow enough to maintain the pressure inside the reactor at a level capable of keeping the reactants liquid phase. It is preferable to place, e.g., a water-cooled condenser between the nozzle and the reactor in order to reflux the reactants which may be entrained by the ammonia back to the reactor.

The process of the present invention may be practiced either batchwise or by a continuous system. The batchwise reaction time depends on the temperature employed, whether the by-product ammonia is removed or not, but usually it is about 2–20 hours.

The present invention will be illustrated by the following examples. All percentages appearing therein are by weight, unless otherwise specified. The abbreviations used are as follows:

TN: m-tolunitrile.
DEA: diethylamine
AA: adipic acid
DTA: N,N-diethyl-m-toluamide.
MTA: N-monoethyl-m-toluamide.
TA: m-toluamide.
tol-A: toluic acid

EXAMPLE 1

A 1-liter autoclave equipped with a stirrer was charged with 250 g (2.14 mols) of meta-tolunitrile, 187.2 g (2.56 mols) of diethylamine, 39.7 g (2.2 mols) of water and 25 g (0.17 mol) of adipic acid as a catalyst. The molar ratio of TN:DEA:$H_2O$ was 1:1.2:1.03. The reaction was performed for 7 hours at 250°C. The reaction product obtained after the reaction weighed 473 g. A gas-chromatographic analysis of the product showed that it contained 2.5% of TN, 37.1% of DTA, 3.9% of MTA, 25.2% of TA, 2.6% of AA and 1.9% of toluic acid. Thus, the yield of DTA based on the consumed TN was 45.2%.

EXAMPLE 2

A 1-liter autoclave equipped with a reflux condensor and a stirrer was charged with the same chemicals as used in Example 1 in the same amounts as in Example 1. The reaction was performed at 250°C. for 7 hours, and during this time, the ammonia gas formed by the reaction was blown through the reflux condenser and a narrowly opened exhaust valve at the upper part of the reflux condenser. The amount of the product obtained was 448 g, and a gas-chromatographic analysis of the product showed that it contained 2.8% of TN, 61.2% of DTA, 2.5% of MTA, 4.1% of TA, 5.3% of AA and 3.1% of toluic acid. Thus, the yield of DTA based on the consumed TN was 70.7%.

EXAMPLE 3

The procedure of Example 2 was repeated except that the reaction temperature was changed to 200°C. The amount of the product obtained after the reaction was 470 g, and a gas-chromatographic analysis of the product showed that it contained 9.7% of TN, 24.0% of DTA, 0.4% of MTA, 25.1% of TA and 3.4% of toluic acid. Thus, the yield of DTA based on the consumed TN was 33.8%.

EXAMPLE 4

The same procedure as in Example 2 was repeated except that the reaction temperature was changed to 225°C. The amount of the reaction obtained after the reaction was 462 g, and a gas-chromatographic analysis of the product showed that it contained 5.2% of TN, 30.1% of DTA, 1.4% of MTA, 24.9% of TA and 3.3% of toluic acid. Thus, the yield of DTA based on the consumed TN was 37.7%.

EXAMPLES 5 to 15

The reaction was performed with varying compositions of the feed under varying reaction conditions while releasing the formed ammonia during the course of the reaction. The feed compositions, the reaction conditions and the results are shown in Table 1. The yield of DTA is based on the consumed TN.

Table 1

| Example No. | Composition of the feed TN:DEA:H₂O:AA | Reaction conditions Temperature (°C.) | Time (hours) | Amount of the reaction product (g) | Results of gas-chromatographic analysis | | | | | TDA yield % |
|---|---|---|---|---|---|---|---|---|---|---|
| | | | | | TN | DTA | MTA | TA | tol-A | |
| 5  | 1.0:1.3:1.1:0.05 | 250 | 10 | 254 | 2.9 | 60.7 | 1.6 | 6.0  | 5.6  | 74.3 |
| 6  | "      :0.10     | "   | "  | 233 | 0.9 | 63.8 | 1.9 | 2.7  | 6.2  | 77.8 |
| 7  | "      :0.15     | "   | "  | 220 | 2.3 | 54.8 | 3.9 | 10.7 | 8.9  | 63.1 |
| 8  | "      :0.10     | 235 | "  | 198 | 3.1 | 69.3 | 1.5 | 5.8  | 4.7  | 71.8 |
| 9  | 1.0:1.5:1.1:0.10 | 250 | "  | 218 | 3.8 | 75.6 | 1.7 | 3.0  | 3.5  | 84.7 |
| 10 | 1.0:1.7:1.1:0.10 | 250 | "  | 224 | 6.7 | 75.1 | 1.9 | 5.1  | 2.9  | 88.0 |
| 11 | 1.0:1.3:1.3:0.10 | 235 | "  | 201 | 4.6 | 63.7 | 1.3 | 8.0  | 8.7  | 67.0 |
| 12 | 1.0:1.5:1.3:0.10 | 240 | "  | 220 | 3.7 | 63.4 | 1.7 | 5.3  | 6.1  | 73.0 |
| 13 | 1.0:1.7:1.3:0.10 | 245 | "  | 227 | 2.7 | 75.7 | 2.0 | 4.1  | 6.5  | 90.0 |
| 14 | 1.0:1.3:1.5:0.10 | 240 | "  | 203 | 1.8 | 71.5 | 1.6 | 10.1 | 15.0 | 76.0 |
| 15 | 1.0:1.5:2.2:0.10 | 230 | "  | 240 | 1.4 | 32.8 | 1.3 | 10.9 | 16.2 | 41.2 |

EXAMPLE 16

A 500-liter autoclave equipped with a reflux condenser and a stirrer was charged with 200 Kg (1.71 Kg-mol) of meta-tolunitrile, 150 Kg (2.05 Kg-mol) of diethylamine, 32 Kg (1.78 Kg-mol) of water and 25 Kg (1.71 Kg-mol) of adipic acid as a catalyst. The molar ratio of TN:DEA:H₂O:AA was 1:1.2:1.04:0.1. The reaction was carried out for 15 hours, and in the same way as in Example 2, the ammonia gas formed was blown from the upper part of the reflux condenser. The amount of the product after the reaction was 350 Kg, and a gas-chromatographic analysis of the product showed that it contained 7.9% of TN, 73.5% of DTA, 1.8% of MTA, 4.0% of TA and 6.2% of toluic acid. Distillation of the product afforded 247 Kg of DTA. The yield of DTA based on the consumed TN was 82.8%.

We claim:

1. A process for the preparation of a N,N-dialkyl-meta (or para)-toluamide, which comprises reacting meta(or para)-tolunitrile with a dialkylamine, with the alkyl group containing 1 to 4 carbon atoms, and water in the liquid phase in the presence of adipic acid as a catalyst at a temperature of 100°–400°C., the amounts of the dialkylamine and water being 0.8–3.0 mols and 0.8–5.0 mols respectively per mol of the tolunitrile and the amount of adipic acid being 0.001–15 mol percent based on the tolunitrile.

2. The process of claim 1 wherein the reaction is carried out while removing from the reaction system the ammonia formed with the progress of the reaction.

3. The process of claim 1 wherein the reaction temperature is 200°–350°C.

4. The process of claim 1 wherein the amounts of the dialkylamine, and water are 1–2 mols and 1–2.5 mols respectively per mol of the tolunitrile and the amount of adipic acid is 0.1–10 mol percent based on the tolunitrile.

* * * * *